(12) United States Patent
Willoughby et al.

(10) Patent No.: US 7,135,292 B2
(45) Date of Patent: Nov. 14, 2006

(54) ANALYSIS AND MODIFICATION OF GENE EXPRESSION IN MARINE INVERTEBRATE CELLS

(75) Inventors: Robin Willoughby, Vero Beach, FL (US); Shirley A. Pomponi, Fort Pierce, FL (US)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 407 days.

(21) Appl. No.: 10/611,113

(22) Filed: Jun. 30, 2003

(65) Prior Publication Data

US 2004/0063119 A1 Apr. 1, 2004

Related U.S. Application Data

(60) Provisional application No. 60/392,626, filed on Jun. 28, 2002.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3
(58) Field of Classification Search .................... 435/6; 536/23.1, 24.3
See application file for complete search history.

(56) References Cited

U.S. PATENT DOCUMENTS 4,729,996 A 3/1988 Wright et al.
5,876,932 A * 3/1999 Fischer ........................... 435/6

OTHER PUBLICATIONS

Lopez et al., J. of Heredity 93 (1) :27-36 (Jan.-Feb. 2002).*
Willoughby et al., In Vitro Cellular and Development Biology Animal, (Mar. 2001) vol. 37, No. 3, Part 2, pp. 21.A. print Meeting Info.: Congress on In Vitro Biology. St. Louis, Missouri, USA, Jun. 16-20, 2001. Society for In Vitro Biology.*
Abdouh, M. et al. "Transcriptional Mechanisms for Induction of 5-$HT_{IA}$ Receptor mRNA and Protein in Activated B and T Lymphocytes" *J Biol Chem*, 2001, pp. 4382-4388, vol. 276, No. 6.
Andrade, P. et al. "Biosynthetic Studies of the Alkaloid, Stevensine, in a Cell Culture of the Marine Sponge *Teichaxinella morchella*" *Tetrahedron Letters*, 1999, pp. 4775-4778, vol. 40, No. 26.
Arosa, F.A. et al. "Calreticulin is Expressed on the Cell Surface of Activated Human Peripheral Blood T Lymphocytes in Association with Major Histocompatibility Complex Class I Molecules" *J. Biol. Chem.*, pp. 16917-16922, vol. 274, No. 24.
Asai, A. et al. "High Level Calcineurin Activity Predisposes Neuronal Cells to Apoptosis" *J. Biol. Chem.*, 1999, pp. 34450-34458, vol. 274, No. 48.
Baldari, C. et al. "Cyclosporin A Blocks Calcium-dependent Pathways of Gene Activation" *J. Biol. Chem.*, 1991, pp. 19103-19108, vol. 266, No. 28.
Batel, R. et al. "Expression of the Human EPB/ERCC-3 Excision Repair Gene-Homolog in the Sponge *Geodia cydonium* after Exposure to Ultraviolet Radiation" *Mutat Res*, 1998, pp. 123-133, vol. 409, No. 3.
Bhat, R. et al. "Reciprocal Expression of Human ETSI1 and ETS2 Genes During T-cell Activation: Regulatory Role for the Protooncogene ETS1" *Proc. Natl. Acad. Sci.*, 1990, pp. 3723-3727, vol. 87, No. 10.
Biesalski et al. "Modulation of myb Gene Expression in Sponges by Retinoic Acid" *Oncogene*, 1992, pp. 1765-1774, vol. 7.
Bohm, M. et al. "The Mitogen-Activated Protein Kinase p38 Pathway is Conserved in Metazoans: Cloning and Activation of p38 of the SAPK2 Subfamily from the Sponge *Suberties domuncula*" *Biol Cell*, 2000, pp. 95-104, vol. 92.
Custodio, M.S. et al. "Primmorphs Generated from Dissociated Cells of the Sponge *Suberties domuncula*: A Model System for Studies of Cell Proliferation and Cell Death" *Mech. Ageing Dev.*, 1998, pp. 45-59, vol. 105.
Fernandez-Busquets, X. et al. "Accumulation in Marine Sponge Grafts of the mRNA Encoding the Main Proteins of the Cell Adhesion System" *J Biol Chem*, 1998, pp. 29545-29553, vol. 273, No. 45.
Foos, G. et al. "Elevated Expression of Ets2 or Distinct Portions of Ets2 can Reverse Ras-Mediated Cellular Transformation" *J. Biol Chem.*, 1998, pp. 18871-18880, vol. 273, No. 30.
Gamulin, V. et al. "Sponge proteins are more similar to those of *Homo sapiens* than to *Caenorhabditis elegans*." *Biological Journal of the Linnean Society*. 2000. vol. 71. pp. 821-828.
Guo, L. et al. "COUP-TF1 Antagonizes Nkx2.5-mediated Activation of the Calreticulin Gene During Cardiac Development" *J. Biol. Chem.*, 2001, pp. 2797-2801, vol. 276, No. 4.
Hess, S.D. et al. "Calcium Oscillations in Human T and Natural Killer Cells Depend upon Membrane Potential and Calcium Influx" *J Immunol*, 1993, pp. 2620-2633, vol. 150, No. 7.
Huang, G. et al. "Gene Expression Profiling of Low-Grade Diffuse Astrocytomas by cDNA Arrays" *Cancer Res.*, 2000, pp. 6868-6874, vol. 60, No. 24.
Jayaraman, T. and Marks, A.R. "Calcineurin is Downstream of the Inositol 1,4,5-Trisphosphate Receptor in the Apoptopic and Cell Growth Pathways" *J. Biol. Chem.*, 2000, pp. 6417-6420, vol. 275, No. 9.
Kageyama, K. et al. "Overexpression of Calreticulin Modulates Protein Kinase B/Akt Signaling to Promote Apoptosis During Cardiac Differntiation of Cardiomyoblast H9c2 Cells" *J Biol Chem*, 2002, pp. 19255-19264, vol. 277, No. 22.
Kihira, H. et al. "Possible Involvement of Calcineurin in Retinoic Acid-Induced Inhibition of Leukemic HL-60 Cell Proliferation" *Int J Oncol*, 1998, pp. 629-634, vol. 12.
Kirillova, I., et al. "Tumor Necrosis Factor Induced DNA Replication in Hepatic Cells Through Nuclear Factor $_{K}$B Activation" *Cell Growth Differ*, 1999, pp. 819-828, vol. 10, No. 12.

(Continued)

Primary Examiner—Ethan Whisenant
(74) *Attorney, Agent, or Firm*—Saliwanchik, Lloyd & Saliwanchik

(57) ABSTRACT

The subject invention identifies changes in gene expression related to treatment of marine invertabret cell cultures.

9 Claims, 5 Drawing Sheets

OTHER PUBLICATIONS

Kitamura, S. et al. "Peroxisome Proliferator-activator Receptor y Induces Growth Arrest and Differentiation Markers of Human colon Cancer Cells" *Jpn. J. Cancer Res.*, 1999, pp. 75-80, vol. 90.

Krasko, A. et al. 1999, "Ethylene Modulates Gene Expression in Cells of the Marine Sponge *Suberties domuncula* and Reduces the Degree of Apoptosis" *J Biol Chem* 274(44):1524-1530.

Krasko, A. et al. "Expression of Silicatein and Collagen Genes in the Marine Sponge *Suberties domuncula* is Controlled by Silicate and Myotrophin" *Eur. J. Biochem.*, 2000, pp. 4878-4887, vol. 267.

Kreuter, M.H. et al. "Inhibition of Intrinsic Protein Tyrosine Kinase Activity of EGF-Receptor Kinase Complex From Human Breast Cancer Cells by the Marine Sponge Metabolite (+)-Aeroplysinin-1" *Comp. Biochem. Physiol.* 1990, pp. 151-158, vol. 97B, No. 1.

Kruse, M. et al. "Differential Expression of Allograft Inflammatory Factor 1 and of Glutathione Peroxidase During Auto—and Allograft Response In Marine Sponges" *J. Cell Sci.*, 1999, pp. 4305-4313, vol. 112.

Kudla, J. et al. 1999 "Genes for calcineurin B-like proteins in *Arabidopsis* are differentially regulated by stress signals" *Proc. Natl. Acad. Sci. USA.* vol. 96, pp. 4718-4723.

Kuhnel, F. et al. "NF$_K$B Mediates Apoptosis Through Transcriptional Activation of Fas (CD95) in Adenoviral Hepatitis" *J. Biol. Chem.*, 2000, pp. 6421-6427, vol. 275, No. 9.

Kulyk, W.M. et al. "Type IX Collagen Gene Expression During Limb Cartilage Differentiation" *Matrix*, 1991, pp. 282-288, vol. 11.

Lennon, G.G., C. Auffray, M. Polymeropoulos and M.B. Soares 1996, "The I.M.A.G.E. Consortium: An Integrated Molecular Analysis of Genomes and Their Expression" *Genomics* 33:151-152.

Matsubara, S. and Ozawa, M. "Expression of a α-catenin-deficient Cells Increases Resistance to Sphingosine-Induced Apoptosis" *J. Cell. Biol.*, 2001, pp. 573-584, vol. 154, No. 3.

Mizunuma, M. et al. "Role of Calcineurin and Mpk1 in Regulating the Onset of Mitosis in Budding Yeast" *Nature*, 1998, pp. 303-306, vol. 392.

Muller, W.E. et al. 2000,"Application of Cell Culture for the Production of Bioactive Compounds from Sponges: Synthesis of Avarol by Primmorphs from *Dysidea avara*" *J Ant Prod* 63(8):1077-1081.

Muller, W.E. et al. "Contribution of Sponge Genes to Unravel the Genome of the Hypothetical Ancestor of Metazoa (Urmetazoa)" *J Ant Prod*, 2000, pp. 1077-1081.

Muller, W.E. et al. "Increased Gene Expression of a Cytokine-Related Molecule and Profilin after Activation of *Suberties domuncula* Cells with Xenogenic Sponge Molecule(s)" *DNA Cell Biol*, 1999, pp. 885-893, vol. 18, No. 12.

Munro M.H. et al. "The Discovery and Development of Marine Compounds with Pharmaceutical Potential" *J Biotechnol*, 1999, pp. 15-25, vol. 70.

Nagata T. et al. "The High Level of hCDC10 Gene Expression in Neuroblastoma may be Associated with Favorable Characteristics of the Tumor" *J. Surg. Res.*, 2000, pp. 267-275, vol. 92, No. 2.

Omay, S.B. et al. "1α,25-Dihydroxyvitamin D$_3$-Induced Upregulation of Calcineurin During Leukemic HL-60 Cell Differntiation" *Blood*, 1996, pp. 2947-2955, vol. 87, No. 7.

Orie, N.N. et al. "Chemoattractant—and Mitogen-Induced Generation of Reactive Oxygen Species in Human Lymphocytes: The Role of Calcium" *Exp Physiol*, 1999, pp. 515-520, vol. 84.

Pahler, S. et al. "Isolation and Characterization of a cDNA Encoding a Potential Morphogen from the Marine Sponge *Geodia cydonium* that is Conserved in Higher Metazoans" *Proc R Soc Lond B Biol Sc.*, 1998, pp. 421-425, vol. 265.

Persson, S. et al. "The $Ca^{2+}$Status of the Endoplasmic Reticulum is Altered by Induction of Calreticulin Expression in Transgenic Plants" *Plant Physiol*, 2001, pp. 1092-1104, vol. 126, No. 3.

Pfeifer, K. et al. "Cloning of the Polyubiquitin cDNA from the Marine Sponge *Geodia cydonium* and its Preferential Expression During Reaggregation of Cells" *J. Cell Sci.* pp. 545-554, vol. 106.

Pomponi, S.A. and R. Willoughby 1994 "Sponge cell culture for production of bioactive metabolites" *In*: van Soest, van Kempen, and Braekman, editors. *Sponges In Time and Space: Biology, Chemistry, Paleontology.* Rotterdam: Balkema. p. 395-400.

Pomponi, S.A. Willoughby, and M. Kelly-Borges 1997a, "Sponge Cell Culture" *In*: Cooksey K, editor. *Molecular Approaches to the Study of the Ocean*. Chapman & Hall. p. 423-429.

Pomponi, S.A. et al. 1997b, "Development of techniques for *in vitro* production of bioactive natural products from marine sponges" *In*: Invertebrate Cell Culture: Novel Directions and Biotechnology Applications. Maramorosch K, Mitsuhashi J, editors. Science Publishers, Inc. p. 231-237.

Pomponi, S.A. et al. 1998. "*In vitro* production of marine-derived antitumor compounds" *In*: Le Gal Y, Halvorson HO, editors. *New Developments in Marine Biotechnology*. New York: Plenum Press p. 73-76.

Ramsay, G. "DNA Chips: State-of-the Art" *Nature Biotechnology*, 1998, pp. 41-44, vol. 16.

Remillard, S.P. et al. "A Calcineurin-B-Encoding Gene Expressed During Differentiation of the Amoeboflagellate *Naegleria gruberi* Contains Two Introns" *Gene*, 1995, pp. 39-45, vol. 154.

Rusnak, F. and Mertz, P. et al. "Calcineurin: Form and Function" *Physiol Rev.*, 2000, pp. 1483-1521, vol. 80, No. 4.

Saito, S. et al. "β-Adrenergic Pathway Induces Apoptosis Through Calcineurin Activation in Cardiac Myocytes" *J. Biol. Chem.*, 2000, pp. 34528-34533, vol. 275, No. 44.

Scheffer et al. "High Conservation of the Serum Response Factor Within Metazoa: cDNA from the Sponge *Geodia cydonium*" *Biological J Linnean Soc*, 1997, pp. 127-137, vol. 61.

Schroder, H.C. et al. "Cloning and Expression of the Sponge Longevity Gene SDLAGL" *Mech Devel*, 2000, pp. 219-220, vol. 95.

Schroder, H.C. et al. "Induction of *ras* Gene Expression by Homologous Aggregation Factor in Cells from the Sponge *Geodia cydonium*" *Biol. Chem.*, 1988, pp. 16334-16340, vol. 263, No. 31.

Sevilla, L. et al. "The Ets2 Transcription Factor Inhibits Apoptosis Induced by Colony-Stimulating Factor 1 Deprivation of Macrophages through a Bcl-$x_L$ -Dependent Mechanism" *Mol. Cell. Biol.*, 1999, pp. 2624-2634, vol. 19, No. 4.

Shou, W. et al. "Exit from Mitosis is Triggered by Tem1-Dependent Release of the Protein Phosphatase Cdc14 from Nucleolar RENT Complex" *Cell*, 1999, pp. 233-244, vol. 97.

Springer, J.E. et al. "Calcineurin-Mediated BAD Dephosphorylation Activates the Caspase-3 Apoptotic Cascade in Traumatic Spinal Cord Injury" *J. Neurosci.*, 2000, pp. 7246-7251, vol. 20, No. 19.

Tian, Q. et al. "Fas-Activated Serine/Threonine Kinase (FAST) Phosphorylates TIA-1 During Fas-Mediated Apoptosis" *J. Exp. Med.*, 1995, pp. 865-874, vo. 182, No. 3.

Tice, D.A. et al. "Synergistic Induction of Tumor Antigens by Wnt-1 Signaling and Retinoic Acid Revealed by Gene Expression Profiling" *J. Biol. Chem.*, 2002, pp. 14329-14335, vol. 277, No. 16.

Tinhofer, I. et al. "Expression of Functional Interleukin-15 Receptor and Autocrine Production of Interleukin-15 as Mechanisms of Tumor Propagation in Multiple Myeloma" *Blood*, 2000, pp. 610-618, vol. 95, No. 2.

Tombal, B. et al. "Thapsigargin Induces a Calmodulin/Calcineurin-Dependent Apoptic Cascade Responsible for the Death of Prostatic Cancer Cells" *Prostate*, 2000, pp. 303-317, vol. 43, No. 4.

Trewavas, A. "Commentary: How Plants Learn" *Proc. Natl. Acad. Sci.*, 1999, pp. 4216-4218, vol. 96.

Uryu, M. et al. "Molecular Cloning of cDNA Encoding Two Subunits of Calcineurin from Scallop Testis Demonstration of Stage-Specific Expression during Maturation of the Testis" *J Biochem*, 2000, pp. 739-746, vol. 127.

Weins et al. "A Homolog of the Putative Tumor Suppressor QM in the Sponge Suberites Domuncula: Downregulation during the Transition from Immortal to Mortal (Apoptotic) Cells" *Tissue Cell*, 1999, pp. 163-169, vol. 31, No. 2.

Willoughby, R. and S.A. Pomponi "Quantitative assessment of marine sponge cells *in vitro*: development of improved growth medium" *In Vitro Cell Dev Biol—Animal*, 2000, pp. 194-200, vol. 36.

Wimmer et al. "Increased Expression of Integrin and Receptor Tyrosine Kinase Genes During Autograft Fusion in the Sponge *Geodia cydonium*" *Cell Adhes Commun*, 1999, pp. 111-1124, vol. 7, No. 2.

Wright, A.E. et al. "3-Amino-1-(2-Aminoimidazolyl)-Prop-1-Ene from the Marine Sponges *Teichazinella morchella* and *Ptilocaulis walpersi*" *J Nat Prod*, 1991, pp. 1684-1686. vol. 54, No. 6.

Pomponi, Shirely A. et al. (Mar. 2001) "Application of DNA Microarray Technology for Gene Discovery and Expression Analysis in a Non-model Organisms" In Vitro Cellular & Development Biology 37(3): p. 21-A, No. 1-1002 (abstract).

Müller, Werner, E.G. et al. (2001) "Contribution of sponge genes to unravel the genome of the hypothetical ancestor of Metazoa (Urmetazoa)" *Gene* 276:161-173.

Schena, Mark et al. (Oct. 20, 1995) "Quantitative Monitoring of Gene Expression Patterns with a Complementary DNA Microarray" *Science* 270:467-470.

\* cited by examiner

```
ttttactatcacaatcaatcaatagatttatcaacctggggctggggctgaccgaggaggtggagggtggcagaggctgggggacaac
cacaggccagggagaaagaggagacagaggaagcaccgagggtgactacgttgtcttccctagatcaattttcttctggatggctcgtg
ctgagtggtagatgagcgaatcgatgagtccagccactgtgaacatgcccccaatgatggcgcacacacctgtcaggaagtgggtgaa
ggacctgtgcttctccgtcagcttcaccatcatgggcgagactcatagaggacgaagactccgggaaggccttggtcgcccaacagcc
cattggcaaccttctcatgtctggtcacagagaactgatttgtcctcagtacctctccgtccaccttcatgtacacagtgggcaccaccttca
caaagtactgg
```

FIG. 3A

```
acatcacaacatcgtttattatgtgaattttttacaatacaaacaaaaaatacagaaatgcaatatatgaatacagctaaatgcagaatggtg
actttttctcttcaagaggccatgattcccatttctagtaaaataaagagactgcatataggtagaaacaggttggtcattagcttcacaattt
tgcctagaaatgatctataaatgcatttccccccctgctacttaccataaagtgtaaaaagggagttaaaggaaagtttccttgttggttccta
ccatatgaaagatgctatattctattttagcagtgccaatatatggaaaatatctaaattaaatgttattacaaaaatgaagcagtaatgagatt
ctggctaaagagggcactaaatgagaataatatatatttaaagaatc
```

FIG. 3B

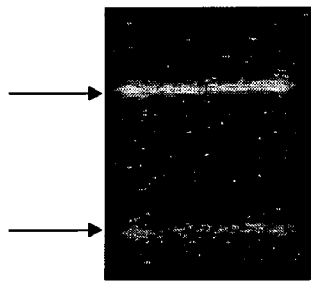

FIG. 4

SEQUENCE LISTING

```
<160> NUMBER OF SEQ ID NOS: 2

<210> SEQ ID NO 1
<211> LENGTH: 457
<212> TYPE: DNA
<213> ORGANISM: Axinella corrugata

<400> SEQUENCE: 1
ttttactatc acaatcaatc aatagattta tcaacctggg gctggggctg accgaggagg        60
tggagggtgg cagaggctgg gggacaacca caggccaggg agaaagagga gacagaggaa       120
gcaccgaggg tgactacgtt gtcttcccta gatcaatttt cttctggatg gctcgtgctg       180
agtggtagat gagcgaatcg atgagtccag ccactgtgaa catgccccca atgatggcgc       240
acacacctgt caggaagtgg gtgaaggacc tgtgcttctc cgtcagcttc accatcatgg       300
gcgagactca tagaggacga agactccggg aaggccttgg tcgcccaaca gcccattggc       360
aaccttctca tgtctggtca cagagaactg atttgtcctc agtacctctc cgtccacctt       420
catgtacaca gtgggcacca ccttcacaaa gtactgg                                457

<210> SEQ ID NO 2
<211> LENGTH: 424
<212> TYPE: DNA
<213> ORGANISM: Axinella corrugata

<400> SEQUENCE: 2
acatcacaac atcgtttatt atgtgaattt tttacaatac aaacaaaaaa tacagaaatg        60
caatatatga atacagctaa atgcagaatg gtgactttt tctcttcaag aggccatgat       120
tcccatttct agtaaaataa agagactgca tataggtaga aacaggttgg tcattagctt       180
cacaattttg cctagaaatg atctataaat gcatttcccc ccctgctact taccataaag       240
tgtaaaaagg gagttaaagg aaagtttcct tgttggttcc taccatatga aagatgctat       300
```

-continued

| | | | | | |
|---|---|---|---|---|---|
| attctatttt | agcagtgcca | atatatggaa | aatatctaaa | ttaaatgtta | ttacaaaaat | 360 |
| gaagcagtaa | tgagattctg | gctaaagagg | gcactaaatg | agaataatat | atatttaaag | 420 |
| aatc | | | | | 424 |

ANALYSIS AND MODIFICATION OF GENE EXPRESSION IN MARINE INVERTEBRATE CELLS

CROSS-REFERENCE TO A RELATED APPLICATION

This application claims the benefit of provisional patent application Ser. No. 60/392,626, filed Jun. 28, 2002, which is hereby incorporated by reference in its entirety.

The subject invention was made with government support under a research project supported by U.S. Department of Commerce, NOAA, National Sea Grant College Program Grant No. NA76RG-0120.

FIELD OF THE INVENTION

The subject invention pertains to the use of stimulation to effect specific changes in gene expression in marine invertebrate cells. This research establishes broad-scale genetic homology among sponges and higher metazoans and it establishes methodology for maximal exploitation of existing knowledge for application to questions in sponge cell biology.

BACKGROUND OF INVENTION

Marine sponges are the focus of biological, chemical and ecological research aimed at understanding and exploiting their unique characteristics. As sessile benthic animals renown for their distinctly elementary metazoan organization, sponges are an exceptional target for studies of self recognition, immunity, and chemical ecology. Many are sources of pharmaceutically important compounds (Faulkner, D. J. 2000, *Nat Prod Rep* 17:1–6). Thus, controlled cellular and molecular studies in sponges present the opportunity to learn more about our multicellular condition, and to understand systems that are sources of compounds with human therapeutic value.

There have been numerous attempts to develop a classic in vitro model (i.e., a cell line) as a tool for marine sponge cell research. While some progress has been made, the ultimate goal of a clonal, axenic, continuously dividing marine sponge cell line has yet to be achieved. Despite this limitation, research is progressing with development of alternative culture systems (Custodio, M. R. et al. 1998, *Mech Ageing Dev* 105(1–2):45–59; Kreuter, M. H. et al. 1992, *Comp. Biochem. Physiol.* 101C(1):183–187; Munro M. H. et al. 1999, *J Biotechnol* 70(1–3):15–25; Muller, W. E. et al. 2000, *J Ant Prod* 63(8):1077–1081), reports of cell proliferation (Krasko, A. et al. 2002, *DNA Cell Biol* 21(1): 67–80), and elucidation of some of the basic cellular and molecular traits of marine sponge cells (Muller, W. E. et al. 2001, *Gene* 276(1–2):161–173; Schutze, J. et al. 2001, *J Mol Evol* 53(4–5):402–415).

One advance is the discovery that marine sponge cells respond to the mitogenic lectin, phytohemagglutinin (PHA) (Pomponi, S. A. and R. Willoughby 1994 "Sponge cell culture for production of bioactive metabolites" In: van Soest, van Kempen, and Braekman, editors. Sponges In Time and Space. Rotterdam: Balkema. p 395–400). Previously, this sponge cell culture phenomenon has been documented only by noting cell numbers, protein content, esterase activity, and DNA content in primary cultures of PHA-treated cells (Willoughby, R. and S. A. Pomponi 2000, "Quantitative assessment of marine sponge cells in vitro: development of improved growth medium" In Vitro Cell Dev Biol—Animal 36:194–200). Even in mammalian cell lines, the molecular basis of the PHA response has been poorly understood, though some recent work has begun to identify some associated molecules.

The Model Sponge

The marine sponge *Axinella corrugata* (Phylum Porifera, Class Demospongiae, Order Axinellida, Family Axinellidae) (FIG. 1) has been used as a model system for more than ten years. It is relatively easy to collect and maintain, and produces the bioactive compound stevensine (Wright, A. E., S. E. Chiles, S. S. Cross 1991, *J Nat Prod* 54(6):1684–1686) (FIG. 2), which has antitumor properties (U.S. Pat. No. 4,729,996) and also functions as a neurotransmitter blocker (Coval, S. J. et al. 1996, U.S. patent application Ser. No. 08/644,138). The production of this compound, which is believed to be of sponge origin, makes *A. corrugata* an appropriate candidate for cell culture studies that focus on biosynthesis as a model for in vitro production of potentially therapeutic products (Andrade, P. et al. 1999, *Tetrahedron Lett* 40(26):4775–4778). Success in establishing primary cell cultures of this species (Pomponi, S. A., R. Willoughby, and M. Kelly-Borges 1997a, "Sponge Cell Culture" In: Cooksey K, editor. Molecular Approaches to the Study of the Ocean. Chapman & Hall. p 423–429; Pomponi, S. A. et al. 1997b, "Development of techniques for in vitro production of bioactive natural products from marine sponges" In: Invertebrate Cell Culture: Novel Directions and Biotechnology Applications. Maramorosch K, Mitsuhashi J, editors. Science Publishers, Inc. p 231–237; Pomponi, S. A. et al. 1998. "In vitro production of marine-derived antitumor compounds" In: Le Gal Y, Halvorson HO, editors. New Developments in Marine Biotechnology. New York: Plenum Press p 73–76) and in vitro production of stevensine (Pomponi et al. 1997b, 1998 supra) have been demonstrated. In addition, *A. corrugata* has been used as an in vitro model for the analysis of the effects of culture medium factors on DNA, protein, and esterase activity (Willoughby and Pomponi 2000 supra).

Marine Sponge Genes and Gene Expression

Previously, some insight into marine sponge potential for molecular response has been achieved by comparing individual sponge nucleic acid sequences to those of model organisms, thus accomplishing gene discovery by database homology analysis.

Many of these previous studies have focused on phylogeny and evolutionary genetics, rather than characterization of in vitro (or even in situ) physiology for functional purposes. Indeed, few have looked at the actual expression of the characterized genes, though a recent contrary trend is evident. In one of the earliest expression studies, Schroder et al. 1988 (*J Biol Chem* 263(31):16334–16340) used immunoprecipitation to quantify ras expression in marine sponge cells. Biesalski et al. 1992 (*Oncogene* 7(9):1765–1774) reported down-regulation of a myb-related gene in cells of *Geodia cydonium*. Also, Pfeifer et al. (1993b, *J Cell Sci* 106 (Pt 2):545–553) reported increased polyubiquitin expression in response to homologous aggregation factor. These studies employed dissociated cells and were therefore an early look at the function of sponge cells in vitro.

More recent studies, many of which utilize intact sponge tissue or re-aggregated cells, include those by Wiens et al. (2000b, *J Mol Evol* 50(6):520–531) and Kruse et al. (1999, *J Cell Sci* 112(part 23):4305–4313), who looked at differential expression in response to allograft rejection in marine sponge tissue. Profilin expression was also up-regulated in the presence of non-self sponge molecules (Muller, W. E. et al. 1999b, *DNA Cell Biol* 1(12):885–893). Potential self-recognition molecules were up-regulated in autografts according to Wimmer et al. (1999b, *Cell Adhes Commun* 7(2):111–1124), Fernandez-Busquets et al. (1998, *J Biol Chem* 273(45):29545–29553), and Blumbach et al. (1999, *Immunogenetics* 9(9):751–763.). Molecules associated with immune responses were reviewed by Muller et al. (1999c, *Transplantation* 68(9):1215–1227.). Scheffer et al. (1997, *Biological J Linnean Soc* 61:127–137) used whole sponges to study SRF expression in response to heat stress. Whole sponges were also used to document increased MA-3 expression (Wagner, C. et al. 1998, *Mar Biol* 131:411–421). Weins et al. (1999a, *Tissue Cell* 31(2):163–169) reported down-regulation of a putative tumor suppressor in response to cadmium exposure, and Krasko et al. (1999, *J Biol Chem* 274(44):1524–1530) reported up-regulation of a protein kinase and a potential ethylene-responsive protein in sponge tissues exposed to ethylene. Utilizing intact tissue, Weins et al. (1999c, *Marine Biol* 133:1–10) documented increased HSP70 and thioredoxin expression in response to 17β-estradiol. Increased HSP70 expression was also noted in response to tributyltin (Batel, R. et al. 1993 *Mar Ecol Prog Ser* 93:245–251.). Phosphorylation of p38 was detected in sponge primmorphs treated with hypertonic medium (Bohm, M. et al. 2000, *Biol Cell* 92:95–104). A similar culture system was used to study differential expression of a longevity assurance-like gene (Schroder, H. C. et al. 2000 *Mech Devel* 95:219–220) as well as collagen and silicatein genes (Krasko, A. et al. 2000 *Eur J Biochem* 267:4878–4887.). Actual cell cultures (not tissue or primmorphs) were once again used to demonstrate ras up-regulation in response to sponge aggregation factor by Wimmer et al. (1999b, *Cell Adhes Commun* 7(2):111–1124.). Intact sponges stressed by exposure to UV light demonstrated increased expression of an excision repair gene homologue as measured by Northern blot comparisons (Batel, R. et al. 1998 *Mutat Res* 409(3):123–33.).

Recently, researchers have begun to directly explore sponge functional genetics in relation to that of other organisms. Muller and colleagues have begun to present multiple cases for genetic homology, as well as functional similarities, between sponges and higher organisms (Muller, W. E. et al. 2001, *Gene* 276(1–2):161–173; Gamulin, V. et al. 2000, *Biological Journal—Linnean Society* 71( ):821–828; Seack, J. et al. 2001, *Biochim Biophys Acta* 1520(1):21–34; Bohm, M. et al. 2000, *Biol Cell* 92:95–104; Wiens, M. et al. 2000a, *Cell Death Differ* 7(5):461–469; Pahler, S. et al. 1998c, *Proc R Soc Lond B Biol Sc.* 265(1394):421–425).

DNA Microarray Technology

DNA microarray technology is relatively new, and is of great interest to the biology community due to its power to simultaneously analyze gene expression for thousands of genes. It offers a functional means to begin to resolve some of the complexities of regulation in biological systems. The technique is based on hybridization of complementary DNA molecules on two-dimensional surfaces upon which thousands of oligonucleotides or DNA fragments (probes) are attached, thus facilitating the simultaneous screening/hybridization of thousands of probes and thousands of targets (Ramsay, G. 1998 *Nature Biotechnology* 16:41–44.).

Since no sponge DNA array currently exists, labeled sponge target molecules were applied to an existing array of human gene sequences. The system uses nylon microarrays and radioactive detection. Since the identities of the probes are known, they provide indications of the identities of the hybridizing sponge gene sequences.

Phytohemagglutinin

Phytohemagglutinin was known for some time as simply a T lymphocyte mitogenic activator (Robbins, J. H. 1964, *Experientia* 20(3):164–168.). More recently, it has been drawn into the explosion of gene expression research following the development of powerful technologies such as microarray analysis. It has now been shown to have mitogenic effects in a number of cell types, including intestinal epithelia (Otte, J. M. et al., 2001, *Digestion* 64(3):169–178.) and fibroblasts (Mustafa, M. et al. 2000, *Cytokine* 12(4):368–373). The details of the genetic response to PHA are beginning to emerge in greater complexity beyond the well-known and long-observed cytokine production response (Janefjord, C. K and M. C. Jenmalm M C. 2001, *Clin Exp Allergy* 31(10):1493–1500; Beppu, R. et al. 2001, *Immunol Invest* 30(2):143–156). The complexity of the immune response is suggested by the finding that PHA stimulation elevates serotonin receptor mRNA levels (Abdouh, M. et al. 2001, *J Biol Chem* 276(6):4382–4388). Broad physiological effects such as elevations in ion transport mRNAs have also been reported (Vereninov, A. A. et al. *Cell Physiol Biochem* 11(1):19–26). Levels of c-fos and c-jun mRNA were elevated 30 minutes after PHA treatment of human lymphocytes (De Palma, L., E. Brown, and R. Baker 1998, *Vox Sang* 75(2):134–138.).

PHA stimulates intracellular signaling pathways related to production of cytokines and cell proliferation. Though details of its action in sponge cell cultures are unknown, it is associated with elevated sponge cell numbers in vitro (Pomponi, S. A. et al. 1997b "Development of techniques for in vitro production of bioactive natural products from marine sponges" In: Invertebrate Cell Culture: Novel Directions and Biotechnology Applications. Maramorosch K, Mitsuhashi J, editors. Science Publishers, Inc. p 231–237).

Receptors. PHA can function in concert with other stimulatory agents and its effects can vary qualitatively according to its concentration (Modiano, J. F. et al. 1999, *Cell Immunol* 197(1):19–29). In addition, multiple isoforms of PHA exist, some of which exhibit different activities in certain cell types (Rebbaa, A. et al. 1996, *J Neurochem* 67(6):2265–2272). The exact role of PHA in receptor activation is still being elucidated. It has been shown to directly bind the epidermal growth factor (EGF) receptor, though details of its function at this site are not clear. Although receptor binding was demonstrated, PHA abrogated expected phenotypic events dependent on EGF receptor signaling in a human cell line (Rebbaa et al. 1996 supra). PHA seems to mimic effects of agents known to function via receptor protein-tyrosine kinases as well as G protein-coupled receptors. It has been shown to modulate both the expression and activity of G protein-coupled receptors (Consorzio et al. 1995; De Blasi A. et al. 1995, *J Clin Invest* 95(1):203–210). The monomeric G protein Ras is activated by PHA, resulting in stimulation of a signaling pathway known to promote T cell proliferation (Downward, J. et al. 1990, *Nature* 364(6286):719–723) and to participate in promotion of interleukin 2 production (Ohtsuka, T., Y. Kazario, and T. Satoh 1996, *Biochim Biophys Acta* 1310(2):223–232). Thus, activation of a variety of receptors by PHA can result in progression of multiple intracellular signals.

Signal Transduction. Specific effects of PHA are consistent with its role in promotion of cell replication and the cell cycle. Induction of immediate-early gene transcription via the AP-1 transcription factor is evident in PHA-induced up-regulation of fos and jun following PHA treatment of lymphocytes (Bulanova, E. G. 1997, *Biochemistry* 62(9):1021–1025). PHA has also been shown to promote mitogen-activated protein kinase activity and G1-phase cyclin-dependent kinase activation (Modiano et al. 1999, *Cell Immunol.* 197(1):19–29). Interleukin 2 production is a well-known result of PHA stimulation in lymphocytes (Mills, G. B. et al. 1990, *J Cell Physiol* 142(3):539–551).

Phospholipid and calcium signals. PHA is known to cause elevations of intracellular free $Ca^{2+}$ in the form of peaks, plateaus, or oscillations associated with initial internal mobilization of calcium from intracellular stores and subsequent influx from outside the cell (Maltsev, V. A. et al. 1994, *Immunol Lett.* 42(1–2):41–47). SH2-type protein tyrosine kinases as well as G-type receptors phosphorylate phospholipase C (PLC) and result in PLC translocation to the cell membrane, initiating a series of intracellular events related to control of cell proliferation (Cooper, G. M. 1997, "The Cell: A Molecular Approach" ASM Press and Sinauer Associates, Inc. 673). Subsequent hydrolysis of phosphatidylinositol 4,5-biphosphate ($PIP_2$) produces diacylglycerol, resulting in activation of protein kinase C and subsequent activation of MAP kinase cascades and/or translocation of NF☐B to the nucleus, where it can mediate transcription of proliferation-associated genes (Kirillova, I., M. Chaisson and N. Fausto 1999, *Cell Growth Differ* 10(12):819–828) as well as genes involved in apoptosis (Kuhnel, F. et al. 2000, *J Biol Chem* 275(9):6421–6427). $PIP_2$ hydrolysis also yields inositol 1,4,5-triphosphate ($IP_3$), which prompts the release of stored $Ca^{2+}$ from the endoplasmic reticulum, initiating a cascade of calcium signaling maintained by calcium influx from outside the cell (Hess, S. D., M. Oortgiesen, and M. D. Cahalan 1993, *J Immunol* 150(7):2620–2633). Sufficient increases in cytosolic calcium result in activation of calmodulin, which in turn activates a variety of proteins including kinases. In concert with calmodulin, calcium and calcineurin B activate the protein phosphatase calcineurin A, resulting in nuclear translocation of the nuclear factor of activated T cells (NFAT), facilitating secretion of interleukin 2 (an autocrine promoter of proliferation) (Mills, G. B. et al. 1990, *J Cell Physiol* 142(3):539–551; Baldari, C. T. et al. 1991, *J Biol Chem* 266(28):19103–19108) and coordination with other transcription factors regulating proliferation (Crabtree, G. R. 1999, *Cell* 96:611–614).

Calcineurin B. Calcineurin B is a regulatory sub-unit that is highly conserved among eukaryotes (Rusnak, F. and P. Mertz 2000, *Physiol Rev* 80(4):1483–1521). Indeed, the amino acid sequences for human and bovine calcineurin B are identical (Nargang, C. E., D. A Bottorff and K. Adachi 1994, *DNA Seq* 4(5): 313–318). Along with calcium and calmodulin, calcineurin B activates the catalytic subunit, calcineurin A (Sugiura, R, S. O. Sio, H. Shunto and T. Kuno 2001, *Cell Mol Life Sci* 58:278–288). Activated calcineurin participates in regulatory functions in multiple cellular processes, including translocation of transcription factors to the nucleus (Masuda, E. S. et al. 1998, *Cell Signal* 10(9):599–611) and control of mitosis (Mizunuma, M. et al. 1998, *Nature* 392(6673):303–306). Differing roles have been observed in mammals, yeasts, and even scallops (Uryu, M. et al. 2000, *J Biochem* 127:739–746). Calcineurin activation is associated with binding of calcium, while calcium elevations are associated with PHA treatment (Orie, N. N. W. Zidek and M. Tepel 1999, *Exp Physiol* 84(3):515–520). In yeast, calcineurin is a requirement for a calcium-induced G2 delay (Mizunuma, M. et al. 1998, *Nature* 392(6673):303–306). In an inverse scenario, increased expression of calcineurin was associated with reduced proliferation in leukemic cells (Kihira, H. et al. 1998, *Int J Oncol* 12(3): 629–634 and Omay, S. B. et al. 1996, *Blood* 87(7):2947–2955) Calcineurin B mRNA levels peak during differentiation of flagellate amoebas (Remillard, S. P. et al. 1995, *Gene* 154(1):39–45). Plant calcineurin B-like protein exhibits increased transcription in response to stress (Kudla, J. et al. 1999, *Proc Natl Acad Sci USA* 96(8):4216–4218). Additional studies implicate calcineurin as a major factor in the execution of apoptotic signals (Springer, J. E. et al. 2000, *J Neurosci* 20(19):7246–7251; Saito, S. et al. 2000, *J Biol Chem* 275(44):34528–34533; Tombal, B. et al. 2000, *Prostate* 43(4):303–317; Jayaraman, T. and A. R. Marks 2000, *J Biol Chem* 275(9):6417–6420; Asai, A. et al., 1999, i 274 (48):34450–34458).

Brief Summary

The subject invention provides materials and methods for evaluating gene expression, identifying new genes, and efficiently producing useful bioactive compounds in marine invertebrate cells.

In one embodiment, the subject invention provides methods for identifying and/or evaluating genes whose expression is regulated by a stimulUS. The stimulus may be, for example, a biochemical including, but not limited to, mitogens and growth factors. Specifically exemplified herein is the use of phytohemagglutin (PHA) as the stimulus.

In a specific embodiment, the method of the subject invention comprises (a) subjecting a cell culture of a marine invertebrate to a biochemical stimulus; (b) thereafter assessing the level of expression of one or more genes in the cell culture; and (c) comparing the level of expression of the gene(s) in the first cell culture with the level of expression of the same gene(s) in a second cell culture of the marine invertebrate, the second cell culture being subjected to no external biochemical stimuli, whereby a difference between the level of expression of the gene(s) in the first cell culture and the level of expression of the gene(s) in the second cell culture is an indication that the gene(s) is regulated by biochemical stimuli.

In one embodiment, the marine invertebrate is a sponge. In an embodiment specifically exemplified herein, the sponge is *Axinella corrugata*.

Also specifically exemplified herein is the use of a cell culture of a group of cells isolated in vivo and cultured in a modified and supplemented commercial growth medium (Willoughby and Pomponi, 2000, supra).

In one aspect, the biochemical stimulus is phytohemagglutin applied for between 5 and 18 hours, preferably about 12 hours.

In one embodiment of the subject invention, the level of expression of the gene(s) is assessed using RNA isolated from the cells, in combination with a nylon membrane microarray technique. In another aspect, the level of expression of the gene is compared by transcriptional profiling following microarray analysis using a radiolabeled probe.

In an embodiment specifically exemplified herein, the method of the subject invention identifies changes in gene expression related to PHA treatment of sponge primary cell cultures. In one embodiment, the subject invention utilizes a cross-species technique in which marine sponge cDNA is hybridized to microarrays of human gene sequences. Widespread specific hybridization is observed.

In accordance with the subject invention, a panel of 108 regulated genes was identified. Two genes with expression differences of similar magnitude, but with reciprocal ratios, were selected for verification by parallel PCR. Results indicate that PHA effects proliferative and anti-apoptotic molecular changes in marine sponge cells.

In accordance with the subject invention, the cross-species microarray technique is an effective tool for gene expression profiling. Close homology between many human and sponge gene sequences has also been discovered.

In one aspect, the subject invention concerns phytohemagglutinin stimulation in sponge cell cultures, and provides methods for improving culture conditions for an in vitro model for studies of metazoan cell biology and production of sponge-derived human therapeutic agents. In this regard, calcium was found to be a factor in both proliferative and stress responses, and that sponge cell culture may be improved by altering the calcium environment in vitro. The subject invention also provides specific genes that may be involved in apoptosis signaling and represent targets for genetic manipulation of the cultures to improve survival and growth.

The subject invention also provides methods for efficient production of bioactive materials. The production of these materials can be increased in accordance with the subject invention by up-regulating gene expression in invertebrate marine cell cultures as described herein.

In a particularly preferred embodiment, the marine invertebrate is a marine sponge and the bioactive product whose production is enhanced is expressed by a gene that naturally occurs in the marine sponge. In an alternative embodiment, the cells of the marine invertebrate cell culture are transformed to express a heterologous gene. In this embodiment, the gene expression of the heterologous gene can be upregulated with a stimulant as described herein.

BRIEF DESCRIPTION OF DRAWINGS

FIGS. 3A and 3B show reference sequences for I.M.A.G.E. clones. FIG. 3A is the sequence for cdc10; FIG. 3B is the sequence for calcineurin B.

FIG. 4 shows the Gel image of total RNA isolated from *A. corrugata*, showing discrete ribosomal RNA bands of appropriate proportional intensity (arrows).

BRIEF DESCRIPTION OF THE SEQUENCES

Figure 1:
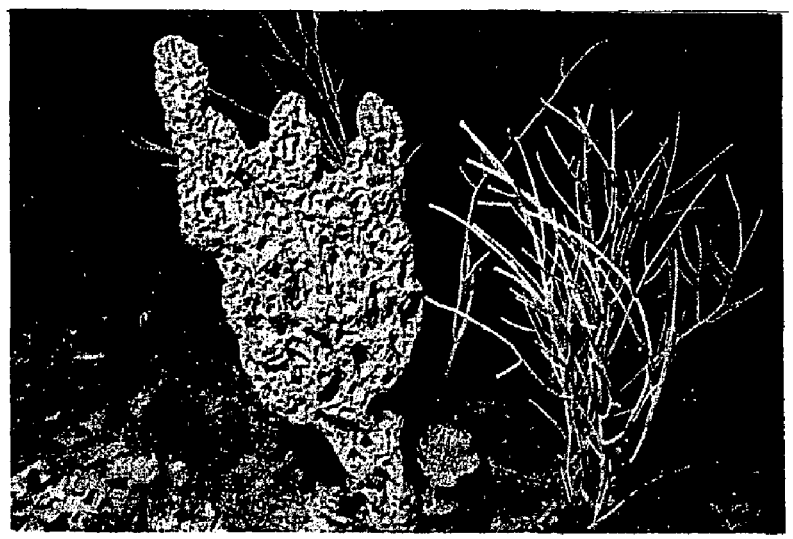
FIG. 1 is the orange sponge, *Axinella corrugata*, in situ.
Figure 2:
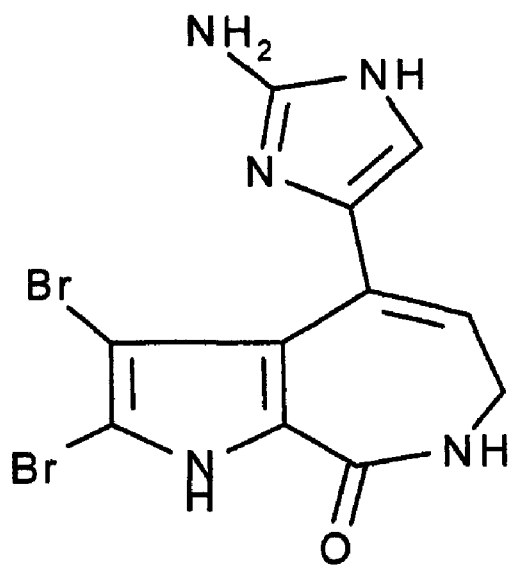
FIG. 2 is the structure of the *Axinella corrugata* bioactive compound, stevensine.

SEQ ID NO:1 is the nucleotide sequence for the reference sequence cdc 10 from *Axinella corrugate* for I.M.A.G.E. clones.

SEQ ID NO:2 is the nucleotide sequence for the reference sequence calcineurin B from *Axinella corrugate* for I.M.A.G.E. clones.

DETAILED DESCRIPTION

The subject invention provides materials and methods for analyzing gene expression, identifying new genes, and efficiently producing useful bioactive compounds in marine invertebrate cells.

In one embodiment, the subject invention provides methods for identifying and/or evaluating genes whose expression is regulated by a selected stimulus. The stimulus may be, for example, a biological factor including, but not limited to, mitogens and growth factors. Specifically exemplified herein is the use of phytohemagglutin (PHA) as the stimulant.

The stimulant, or stimulus, used according to the methods of the subject invention can be any factor that has an effect on gene expression. Many such factors are well known in the art and include biochemical molecules as well as physical stimuli such as hydrodynamic forces, light, temperature, pressure, and radiation. Biochemical factors include, but are not limited to, mitogens, growth factors, hormones, and cytokines.

Although reference is made herein to the use of "stimuli" or "stimulants", it should be understood that the administration of these agents may, as described herein, result in either up- or down-regulation of expression of genes.

In a specific embodiment, the method of the subject invention comprises (a) subjecting a cell culture of a marine invertebrate to biochemical stimulation; (b) thereafter assessing the level of expression of one or more genes in the cell culture; and (c) comparing the level of expression of the gene(s) in the first cell culture with the level of expression of the same gene(s) in a second cell culture of the marine invertebrate, the second cell culture being subjected to no external biochemical stimuli, whereby a difference between the level of expression of the gene(s) in the first cell culture and the level of expression of the gene(s) in the second cell culture is an indication that the gene(s) is regulated by biochemical stimuli.

Marine invertebrates that can be used according to the subject invention include any such animals whose cells can be grown in vitro. Such marine invertebrates are well known to those skilled in the art.

In one embodiment, the marine invertebrate is a sponge. In an embodiment specifically exemplified herein, the sponge is *Axinella corrugata*.

The marine sponge *Axinella corrugata* is a model for cell culture development and is known to respond to phytohemagglutinin (PHA) stimulation in vitro. In one embodiment, the subject invention identifies changes in gene expression related to PHA treatment of sponge primary cell cultures. In a specific embodiment, the subject invention utilizes a cross-species technique in which marine sponge cDNA is hybridized to microarrays of human gene sequences. Widespread specific hybridization is observed.

A panel of 108 potentially regulated genes was identified. Two genes with expression differences of similar magnitude, but with reciprocal ratios, were selected for verification by parallel PCR. Results indicate that PHA effects proliferative and anti-apoptotic molecular changes in marine sponge cells.

In accordance with the subject invention, the cross-species microarray technique is an effective tool for gene expression profiling. Close homology between many human and sponge gene sequences has also been discovered.

In one aspect, the subject invention concerns phytohemagglutinin stimulation in sponge cell cultures, and provides methods for improving culture conditions for an in vitro model for studies of metazoan cell biology and production of sponge-derived human therapeutic agents. In this regard calcium was found to be a factor in both proliferative and stress responses, and that sponge cell culture may be improved by altering the calcium environment in vitro. The subject invention also provides specific genes that may be involved in apoptosis signaling and represent targets for genetic manipulation of the cultures to improve survival and growth.

The subject invention also provides methods for efficient production of bioactive materials. The production of these materials can be increased in accordance with the subject invention by up-regulating gene expression in invertebrate marine cell cultures as described herein.

In a particularly preferred embodiment, the marine invertebrate is a marine sponge and the bioactive product whose production is enhanced is expressed by a gene that naturally occurs in the marine sponge. In an alternative embodiment, the cells of the marine invertebrate cell culture are transformed to express a heterologous gene. In this embodiment, the gene expression of the heterologous gene can be upregulated with a stimulant as described herein.

The bioactive products produced by the cells of subject invention can be readily isolated and purified, if desired, using standard procedures well known and easily practiced by those skilled in the art.

In specific embodiments, the subject invention concerns the following aspects:
1. Preparation of functional labeled targets from *Axinella corrugata* for application to microarrays.
2. Development of effective hybridization protocols for application of marine sponge samples to existing (cross-specific) microarrays.
3. Identification of homologies to known genes via microarray hybridization.
4. Detection of differential expression of gene homologues.
5. Correlation of altered gene expression with applied cell culture techniques in order to identify and characterization of factors that inhibit or promote continued in vitro replication.

General Experimental Design

Human sequence microarrays were used to compare gene expression in untreated and PHA-treated *A. corrugata* cell cultures. The use of human reference sequences assured the inclusion of many genes that were clearly identified, functionally characterized, and well studied. Statistical methods reduced the data pool to a set of those gene sequences displaying the most significant expression differences.

Materials and Methods

Culture Methods

Sponge Cells. Cells were obtained from cryopreserved stocks at Harbor Branch Oceanographic Institution. All cells were derived from *Axinella corrugata* specimens collected in the waters of Florida, the Bahamas, and the Caribbean Sea, and were cryopreserved according to Pomponi et al. (Pomponi et al. 1997b supra). This sponge is relatively common and easy to collect, amenable to culture efforts, and produces the bioactive compound, stevensine, in vitro (Pomponi et al. 1997b supra). Enriched fractions of dissociated sponge cells were prepared, cryopreserved, and thawed according to previously published methods (Pomponi et al. 1997b supra). Cells were incubated at 22–25° C. in a growth medium consisting of a modified and supplemented commercial formulation (Willoughby and Pomponi 2000 supra). The length of the incubation period was based on my unpublished observation of elevated DNA and protein contents (9%, P=0.034, and 9%, P=0.038, respectively) in PHA-treated cultures, according to fluorescent assays of 6 replicate comparisons (Willoughby and Pomponi 2000 supra). Since the effects were observed between 6 and 18 hours after treatment, cells were cultured for 12-hour periods representing the center point of the period of observed changes. Two sets of cultures were incubated with approximately $2\times10^8$ cells per T-75 flask—a control set and an experimental set treated with 1.5% phytohemagglutinin (PHA) (Life Technologies, M-form).

Murine Cells. Following the same experimental design as described for sponge cells, TIB-155 murine lymphocytes were cultured in the American Type Culture Collection-specified growth medium (RPMI 1640 with 0.05 mM 2-mercaptoethanol and 10% fetal bovine serum).

Nucleic Acid Preparation

RNA Isolation. RNA isolation was performed on unrinsed, pelleted cells. Pellets were quickly frozen in a dry ice alcohol bath and stored at −70° C. until RNA isolation. The Qiagen RNeasy® protocol was used, with the following modifications. Samples were disrupted with a micropestle or homogenized by the rotor-stator method, using twice the recommended volume of lysis solution. Prior to column loading, samples were centrifuged through a Qiashredder® column to complete homogenization and remove insoluble material. Supernatant was collected for use in the rest of the protocol. During the first wash step, samples were incubated on the column with DNase 1 (Qiagen or Ambion) for 15 minutes. After the final wash, samples were incubated on the column with the RNase free elution water for 15 minutes prior to elution. Sub-samples were diluted 20× and quantified on a Genequant® spectrophotometer.

Additional sub-samples were incubated with loading dye and subjected to denaturing agarose gel electrophoresis for assessment of RNA integrity (1.2% agarose formaldehyde gel, per Ambion NorthernMax protocol). RNA not displaying a darker large ribosomal band was discarded. Samples were held in a bench-top cooler for a maximum of 1 hour prior to reverse transcription.

cDNA Labeling. Sub-samples of the isolated total RNA (8 μl) were primed with oligo dT (10–20 mer) (Research Genetics, Inc.) for 10 minutes at 70° C., then briefly chilled on ice, followed by addition of 2 volumes of RT cocktail based upon the Life Technologies Superscript II® protocol (containing dATP, dGTP, dTTP, and α-$^{33}$P dCTP [NEN Easy Tides®, 3000 Ci/mmol]). The mixture was incubated for 90 minutes at 37° C., and diluted to 100 μl for purification on a Bio-Spin column (Boi-Rad) according to the Gene Filter® (Research Genetics, Inc.) recommended protocol. The resultant labeled probes were then denatured for 3 minutes in a boiling water bath prior to incorporation into the hybridization solution.

Microarray Analyses

Microarrays. Research Genetics Gene Filters®, version 211, were employed in this study. These microarrays feature over 4000 distinct sequence-verified genes spotted onto a 5×7 cm nylon membrane. The DNA at each spot represents approximately 1 kb from the 3' end of the gene. The microarrays also include spots of total genomic DNA (see FIG. 5). The 211 series is constructed from human sequences. A cross-referenced database listing of all the genes represented on the array is available at http://www.resgen.com. The 2 genes referenced in this work carry the I.M.A.G.E. Consortium (Lennon, G. G., C. Auffray, M. Polymeropoulos and M. B. Soares 1996, *Genomics* 33:151–152), Clone IDs 81408 (calcineurin B) and 858292 (cdc10).

Hybridization. Gene Filters® were pre-hybridized with blocking agents (5 μl each Cot-1 DNA and poly dA [Research Genetics, Inc.]) in 5 ml Microhyb® (Research Genetics, Inc.) at 42° C. for 2 hours at 8 rpm in a mini hybridization oven. After addition of the probe, hybridization proceeded for 12–18 hours at 42° C. The first wash was for 20 minutes at 50° C. with 2×SSC and 1% SDS (30 ml total volume). This wash was then repeated a second time. The final wash was for 45 minutes at 55° C. in 0.5×SSC and 1% SDS (100 ml total volume).

Imaging. Washed membranes were placed on dampened filter paper and wrapped in a single layer of Glad Wrap®. Membranes were exposed to a Packard MP phosphor storage screen for varied time periods, ranging from a few hours to 3 days. Target signal strengths for the final images were for a background less than 15 (preferably less than 12) and a maximum intensity less than 30,000 (arbitrary units, Optiquant® [Packard Instruments] imaging software). Images were scanned at 600 dpi on a Packard Cyclone® phosphorimager, and exported into Research Genetics Pathways® software.

Data Management. Quantitative values for each data point were exported into an Excel spreadsheet. Total genomic spots were not included in the analysis. The background intensity was subtracted from each value. Some points fell slightly below background, and were assigned a value of zero. Each data point (with background subtracted) was normalized by expression as a percent of the average intensity. In the absence of a cell line, cryopreserved stocks from several specimens were used, no doubt resulting in differences from one replication to the next. Samples were grouped as replicate pairs, each matched by specimen and cell culture, comprising 2 populations, control and treated, of 8 samples each. Any gene with a ratio of means less than 2, and/or a mean greater intensity less than 10% above background intensity, was not considered a candidate for significance. To determine significance, the data were transformed to natural logarithms (Zar, J. H. 1974, "Biostatistical Analysis" Prentice-Hall Inc., p. 620; Motulsky, H. 1995 "Intuitive Biostatistics" Oxford University Press, p. 408) and subjected to a two-tailed paired t test (Motulsky 1995 supra). Any data point yielding a P value less than 0.05 was considered potentially significant.

Data self-test. Each of the two data sets (control and PHA-treated) were compared to themselves by randomly splitting each of them into two groups of four. The two paired groups of four values each were then subjected to the same data filters and t test as described above (Motulsky 1995 supra). This yielded two additional sets of self-test results. These data indicate the inherent variation among cell cultures receiving the same treatment. To compare results for the same sample size as the self test, a paired t test was run using only 4 of the 8 values in each of the control and PHA data sets.

PCR Amplification cDNA Preparation. cDNA was prepared as described in the array experiments, using unlabeled dCTP instead of the α-$^{33}$P dCTP. The final product was then diluted 25-fold in water, loaded onto a DNA recovery column (Zymo Research D4001) and washed according to the manufacturer's protocol followed by elution with four consecutive 25-μl aliquots of nuclease free water. The procedure was then repeated for 40-μl aliquots, with a final elution in two aliquots of 20 μl, to produce twice-washed cDNA. Final template solution was prepared from 10 μl of twice-washed cDNA by addition of 80 μl water and precipitation with 30 μl 5M ammonium acetate and 250 μl ethanol at −20° C. for 30 minutes. Samples were centrifuged at 4° C. for 30 minutes at 10,000× g. Pellets were washed twice with 70% ethanol and air-dried for 15 minutes prior to resuspension in 20 μl nuclease free water. For the -RT control reactions, RNA/DNA template amounts were calculated volumetrically, to correspond with the volume of final template used in each reaction. Since some loss of cDNA can be expected for each of the purification steps, the volume of template used in the -RT control reactions likely exceeds that used in the corresponding test reactions, resulting in overestimation of the possible contribution of DNA background signals, acting as a conservative control.

Reference Clone Cultures. Reference plasmid clones (Research Genetics, Inc.) were cultured at 37° C. in LB Broth Lennox (Difco). DNA was extracted from culture pellets with the Sigma-Aldrich GenElute Plasmid Miniprep kit, according to the manufacturer's protocol.

Primers. The reference sequences in the I.M.A.G.E. clone collection (FIG. 3) were used for primer design. For the calcineurin B sequence, primers were as follows: 5' atgagaaggttgccaatg 3' and 5'atgcccccaatgatggcgca 3'. This primer set predicted a 150 bp product. For the cdc-10 sequence, primers were as follows: 5' ctctttagccagaatctc 3' and 5' acaggttggtcattagc 3'. This primer set predicted a 228 bp product.

CR Amplification Reactions. The polymerase chain reaction was performed in an MJ Research PTC-150 Minicycler thermal cycler with "hot bonnet". Each reaction utilized 1 μl of final template in a 25 μl total reaction volume. Promega PCR Master Mix (M7501) was used according to protocol. Primers were at 400 nM final concentration. The cycling program was the same for each sequence: 95° C. for 2 minutes for initial denaturation, followed by 37 cycles of 95°

C. for 60 seconds, 55° C. (calcineurin) or 52° C. (cdc10) for 80 seconds, and 72° C. for 60 seconds. Final extension was at 72° C. for 10 minutes.

Gel Electrophoresis. PCR products were diluted with 0.2× volume Research Genetics 6× Gel Loading Buffer (750005) and loaded directly into the wells of a 3% agarose gel (Ambion LE agarose) (40 ml 0.5×TBE), using equal loading volumes for paired treated/untreated samples. Running time was 30 minutes in 0.5×TBE. Bands were visualized by staining for 20 minutes in 2 ng/ml ethidium bromide, de-staining twice in distilled water for 15 minutes, and imaging with UV transillumination and a Stratagene Eagle Eye digital imager.

Methods Strategy Summary

The procedures described above are complementary and offer specific advantages for data interpretation. Most importantly, the procedures are not particularly sensitive to slight differences in the starting amounts of RNA. The microarray hybridization data are expressed using a normalized intensity that indicates expression levels relative to the expression levels of other genes, rather than as an absolute value. Similarly, the PCR experiments were designed for genes showing opposite regulation of similar magnitude, for comparison of relative expression levels. Each gene thus served as an endogenous control for the other. The results serve well to corroborate the microarray data in terms of expression ratios and to verify the existence of the target sequences. The microarray data are the stronger indicators of the expression ratios, while the PCR data better validate the human-sponge sequence homologies.

Following are examples which illustrate procedures for practicing the invention. These examples should not be construed as limiting. All percentages are by weight and all solvent mixture proportions are by volume unless otherwise noted.

EXAMPLE 1

Microarray Analysis

General Considerations. Though RNA sometimes exhibited signs of degradation and was discarded, FIG. 4 shows an example of intact sponge RNA. Ideally, the ribosomal band ratio (large/small) should be close to 2 for intact RNA. In most cases, ratios were between 1.6 and 2, indicating relative preservation of the RNA. Purity was generally indicated by an absorbance ratio greater than 1.8. However, samples occasionally exhibited ratios as low as 1.6.

In the interest of using the least degraded product, freshly isolated RNA was put directly into the reverse transcription reaction without interim precipitation. This avoided a slight drop in integrity associated with precipitation and resuspension. Generally, between 0.2 and 1 µg of RNA (matched for paired samples) were used for each reverse transcription, with most experiments conducted at the lower end of the range, since the size of sponge cell cultures required to produce larger quantities was prohibitive. Reverse transcription was consistently successful, resulting in labeled cDNA. After column purification, probe activities ranged from 5 to 10 million dpm.

Figures 5A, 5B:
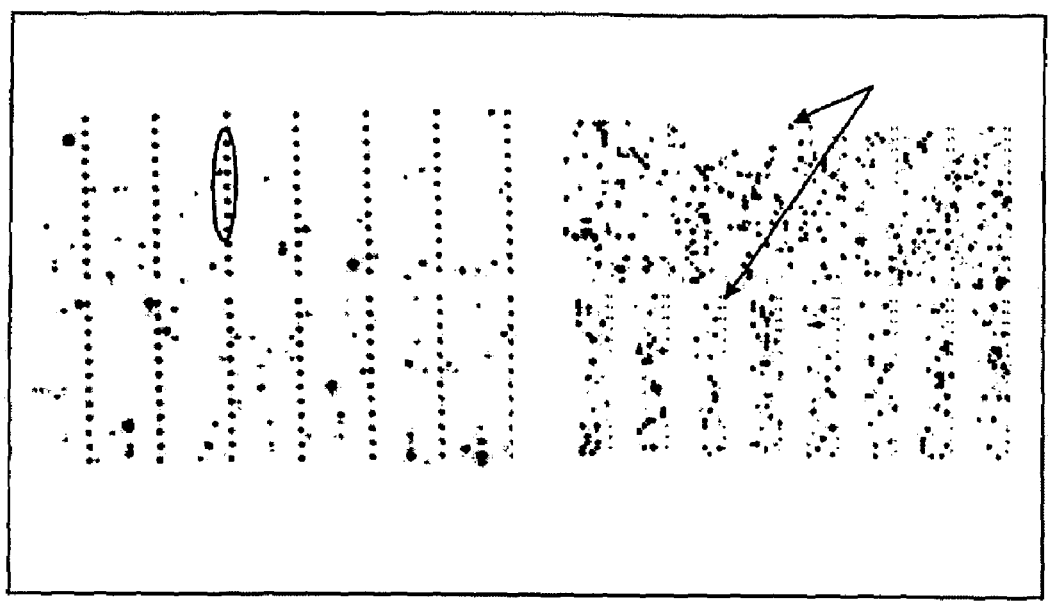
FIGS. 5A and 5B show phosphorimages of $^{33}$P-labeled *A. corrugata* cDNA reverse transcribed from degraded (FIG. 5A) and intact (FIG. 5B) RNA, and hybridized to Gene Filters® (Gene Filter® versions are not identical so the gene sets and locations differ). Note rows of relatively intense signals from total genomic DNA spots with degraded sample (example with ellipse, FIG. 5A). Equivalent spots (FIG. 5B) appear as low intensity columns/double columns with the intact sample (arrows).

Following hybridization, the exposed images were of high quality, and revealed widespread differential hybridization and the maintenance of the integrity of the RNA. FIG. 5 contrasts two Gene Filter® images. FIG. 5A was obtained using degraded RNA. The result is that the total genomic DNA spots "stand out" relative to the data points. This is not the case for FIG. 5B, which was obtained with intact RNA, and is representative of the array images used for this study.

Figure 6:
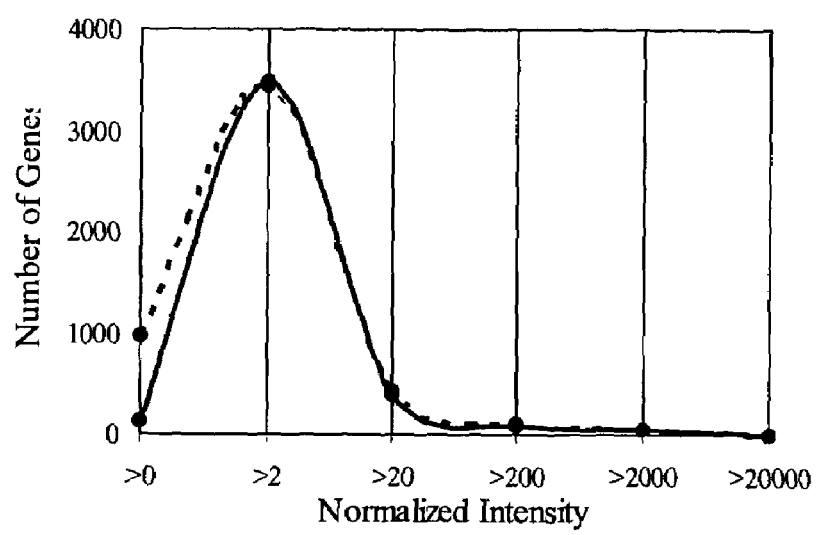
FIG. 6 shows an abundance distribution curve. Normalized intensities for arrayed genes were categorized by intensity level and a curve drawn through the plotted points. Solid line, control samples, broken line, PHA samples. Vertical broken line represents approximate intensity minimum for the panel of 108 genes.
Figure 7A:
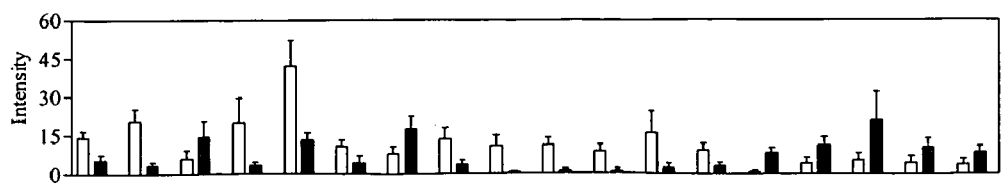
FIGS. 7A–7F show a panel of 108 statistically significant regulated human gene homologues in *A. corrugata* (P</=0.05). Intensity normalized as % of average. Open bars represent untreated control cultures. Filled bars represent PHA treated cultures. Mean+sem. N=8. Most genes are expressed at below-average intensities. Highly expressed genes are shown in the lower panel (note varied y axes indicating a range of expression levels).
Figure 7B:
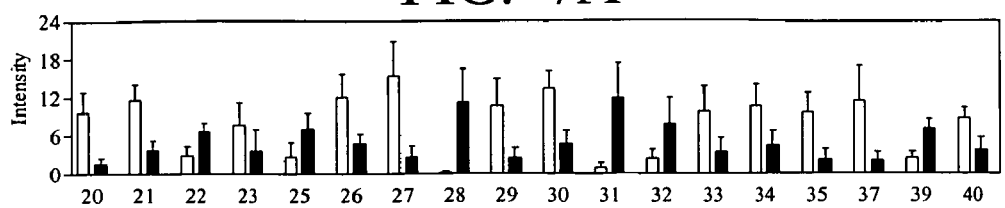
Figure 7C:
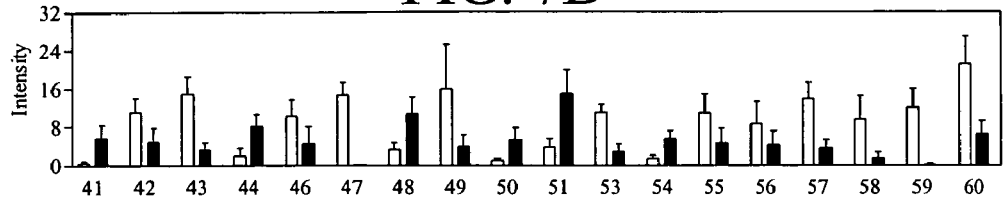
Figure 7D:
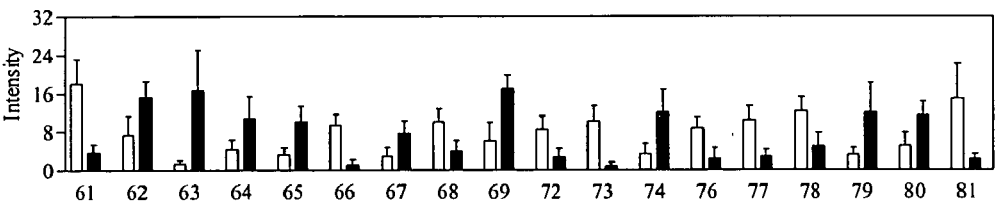
Figure 7E:
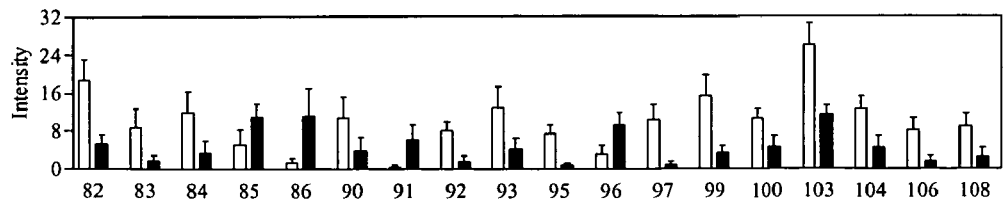
Figure 7F:
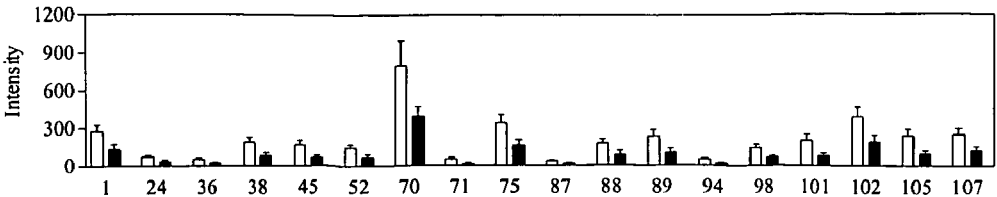

Abundance Distribution. FIG. 6 shows a curve plotted through 5 points indicating the number of arrayed genes exhibiting a given minimum signal intensity. These expression level categories group the genes according to their relative signal intensity, which is representative of the number of molecules hybridized at a given arrayed spot and therefore represents the relative abundance of the specific mRNA in the total RNA pool. As expected, most of the genes are expressed at very low levels (less than 20% of the average intensity on the array). The vertical broken line in FIG. 6 represents the approximate location of the signal intensity threshold used in this study. Though the threshold clearly admits some of these lower abundance genes for significance consideration, most of the low-intensity signals were excluded.

Cell Culture Differentials. A group of 108 data points met the criteria established for data management methods. Most of these genes were of below average expression intensity. Data for these genes are shown in FIG. 7 and Table 1. Tables 2 and 3 indicate the genes displaying the greatest up-regulation (ratio >10) and the greatest down-regulation (ratio <0.1), respectively.

TABLE 1

Potentially regulated genes by category.
Numbers correspond to FIG. 7.

| Gene/Category | Ratio | P Value | No. |
| --- | --- | --- | --- |
| Cell cycle | | | |
| Cell division cycle 10 (homologous to CDC10 of S. cerevisiae | 2.302 | 0.032 | 22 |
| H. sapiens mRNA for M-phase phosphoprotein, mpp5 | 2.970 | 0.031 | 39 |
| Homo sapiens cdc14 homolog mRNA, complete cds | 11.905 | 0.019 | 63 |
| Cytokines/immunity | | | |
| MHC class II DQ-beta associated with DR2, DQw1 protein | 0.492 | 0.018 | 1 |
| Interleukin 7 receptor | 0.156 | 0.015 | 5 |
| Membrane metallo-endopeptidase (neutral endopeptidase, enkephalinase, CALLA, CD10) | 0.169 | 0.049 | 20 |
| Homo sapiens mRNA for ISLR, complete cds | 12.597 | 0.024 | 41 |
| H. sapiens mRNA for M130 antigen | 0.443 | 0.019 | 42 |
| Interleukin 15 receptor alpha chain | 3.996 | 0.030 | 54 |
| Small inducible cytokine A11 (eotaxin) | 0.493 | 0.035 | 56 |
| Major histocompatibility complex, class II, DR beta 5 | 0.255 | 0.011 | 57 |
| H. sapiens mRNA for p40 | 7.841 | 0.012 | 86 |
| Cytoskeletal/motility | | | |
| RhoE | 0.312 | 0.027 | 60 |
| Human capping protein alpha mRNA, partial cds | 2.650 | 0.040 | 67 |
| Human alpha-tubulin isotype H2-alpha gene, last exon | 0.264 | 0.032 | 77 |
| Human alpha-cardiac actin gene, 5' flank and | 0.402 | 0.029 | 78 |
| Villin | 0.008 | 0.000 | 47 |
| Development | | | |
| Human bone morphogenetic protein-3b | 0.209 | 0.018 | 61 |
| Human cartilage-specific homeodomain protein Cart-1 mRNA, complete cds | 0.201 | 0.038 | 92 |
| ECM/adhesion | | | |
| Collagen, type II, alpha 1 (primary osteoarthritis, spondyloepiphyseal dysplasia, congenital) | 0.384 | 0.040 | 2 |
| Collagen, type V, alpha | 0.137 | 0.044 | 13 |
| Collagen, type IX, alpha 3 | 47.686 | 0.036 | 28 |
| Cadherin 11 (OB-cadherin) | 0.425 | 0.032 | 55 |

TABLE 1-continued

Potentially regulated genes by category.
Numbers correspond to FIG. 7.

| Gene/Category | Ratio | P Value | No. |
|---|---|---|---|
| Homo sapiens thrombospondin 3 (THBS3) gene, complete cds | 0.019 | 0.003 | 59 |
| Human mRNA for alpha-catenin, complete cds | 0.147 | 0.025 | 81 |
| Homo sapiens, alpha-1 (VI) collagen | 2.509 | 0.028 | 64 |
| Keratin, type I cytoskeletal 20 | 0.283 | 0.032 | 84 |
| Estrogen response | | | |
| Human HEM45 mRNA, complete cds | 0.114 | 0.046 | 95 |
| H. sapiens mRNA for 17-beta-hydroxysteroid dehydrogenase | 0.432 | 0.040 | 100 |
| G proteins/regulation | | | |
| Alternative guanine nucleotide-binding regulatory protein (G) alpha-inhibitory-subunit | 0.462 | 0.012 | 52 |
| Ras-like protein TC21 | 2.737 | 0.019 | 69 |
| Homo sapiens mRNA for transducin (beta) like 1 protein | 0.091 | 0.005 | 97 |
| Growth factors/regulation | | | |
| Homo sapiens mRNA for epiregulin, complete cds | 0.101 | 0.028 | 12 |
| Homo sapiens TNF-alpha stimulated ABC protein (ABC50) mRNA, complete cds | 3.865 | 0.023 | 17 |
| Human BTG2 (BTG2) mRNA, complete cds | 2.431 | 0.014 | 19 |
| Heat shock | | | |
| Heat shock 60 kD protein 1 (chaperonin) | 2.443 | 0.035 | 4 |
| Homo sapiens DnaJ protein (HSPF2) mRNA, complete cds | 0.206 | 0.040 | 83 |
| Human disease | | | |
| Human renal cell carcinoma antigen RAGE-1 mRNA, complete putative cds | 0.477 | 0.039 | 23 |
| MpV17 transgene, murine homolog, glomerulosclerosis | 0.319 | 0.032 | 14 |
| Von Hippel-Lindau syndrome | 2.707 | 0.013 | 16 |
| Fanconi anemia complementation group C | 0.342 | 0.044 | 33 |
| Autosomal dominant polycystic kidney disease type II | 0.224 | 0.021 | 35 |
| 6-Pyruvol tetrahydrobiopterin synthase | 0.440 | 0.032 | 46 |
| Metabolic/housekeeping/miscellaneous | | | |
| Cytochrome P450, subfamily IVA, polypeptide 11 | 0.310 | 0.013 | 6 |
| Human metallothionein I-B gene | 0.388 | 0.030 | 7 |
| Tissue inhibitor of metalloproteinase 1 (erythroid potentiating activity, collagenase inhibitor) | 0.252 | 0.037 | 9 |
| Adenylate kinase 1 | 0.055 | 0.027 | 10 |
| Tyrosine 3-monooxygenase/tryptophan 5-monooxygenase activation protein, zeta polypeptide | 9.835 | 0.013 | 15 |
| Metabolic/housekeeping/miscellaneous | | | |
| Human brain mRNA for photolyase homolog, complete cds | 2.486 | 0.026 | 18 |
| Homo sapiens putative OSP like protein mRNA, partial cds | 0.491 | 0.013 | 24 |
| H. sapiens mRNA for phosphate cyclase | 0.395 | 0.041 | 26 |
| Triosephosphate isomerase 1 | 0.357 | 0.038 | 30 |
| Zinc finger protein basonuclin | 0.417 | 0.039 | 34 |
| Double-stranded RNA adenosine deaminase | 0.456 | 0.000 | 36 |
| Dual specificity protein phosphatase PAC-1 | 0.175 | 0.036 | 37 |
| Homo sapiens Tax interaction protein 33 mRNA, partial cds | 0.426 | 0.009 | 38 |
| Human tRNA-guanine transglycosylase mRNA, complete cds | 0.213 | 0.017 | 43 |
| Homo sapiens mRNA for vesicle associated membrane protein 2 (VAMP2) | 3.925 | 0.050 | 44 |
| Multidrug resistance protein 1 | 3.272 | 0.037 | 48 |
| Human histone H2B.1 mRNA, 3' end | 0.247 | 0.020 | 49 |
| Amyloid P component, serum | 3.994 | 0.032 | 51 |
| Ribosomal protein S6 kinase, 90 kD, polypeptide 2 | 0.252 | 0.013 | 53 |
| Vitamin K-dependent gamma-B74carboxylase | 2.101 | 0.026 | 62 |
| Homo sapiens BAI 3 mRNA, complete cds | 3.228 | 0.027 | 65 |
| Homo sapiens mRNA for inositol 1,4,5-trisphosphate 3-kinase isoenzyme, partial cds | 0.494 | 0.037 | 70 |
| Homo sapiens clone 23619 phosphoprotein mRNA, partial cds | 0.296 | 0.036 | 71 |
| Human lysosomal glycosylasparaginase (AGA) gene | 0.317 | 0.018 | 72 |
| Homo sapiens mRNA for repressor protein, partial cds | 0.483 | 0.042 | 75 |
| N-Terminal acetyltransferase complex ARD1 subunit homolog + B88 | 0.275 | 0.001 | 76 |
| Homo sapiens mRNA for p115, complete cds | 0.477 | 0.004 | 87 |
| Factor VIII intron 22 protein | 0.490 | 0.031 | 88 |
| Human RNA polymerase II subunit hsRPB7 mRNA, complete cds | 0.441 | 0.016 | 89 |
| Homo sapiens mRNA for osteomodulin, complete cds | 0.354 | 0.008 | 90 |
| Metabolic/housekeeping/miscellaneous | | | |
| Human cytochrome bc-1 complex core protein II mRNA, complete cds | 0.325 | 0.019 | 93 |
| C-1-tetrahydrofolate synthase, cytoplasmic | 2.966 | 0.009 | 96 |
| H. sapiens mRNA for InsP3 5-phosphatase | 0.215 | 0.031 | 99 |
| Ubiquitin carboxyl-terminal hydrolase isozyme L3 | 0.388 | 0.005 | 101 |
| Human putative tRNA synthetase-like protein mRNA, complete cds | 0.493 | 0.041 | 102 |
| Human galectin-4 (GAL4) mRNA, complete cds | 0.443 | 0.036 | 103 |
| Glycylpeptide N-tetradecanoyl transferase | 0.354 | 0.020 | 104 |
| H. sapiens LDLC mRNA | 0.395 | 0.010 | 105 |
| Human enigma gene, complete cds | 0.496 | 0.025 | 107 |
| Human FEZ2 mRNA, partial cds | 0.283 | 0.042 | 108 |
| Neurological | | | |
| Oxytocin receptor | 0.084 | 0.021 | 11 |
| Human mRNA for prepro cortistatin like peptide, complete cds | 3.616 | 0.024 | 74 |
| Homo sapiens FMRFamide-related prepropeptide mRNA, complete cds | 2.156 | 0.042 | 85 |
| Oncogenesis/apoptosis | | | |
| Nucleolysin TIA-1 | 0.430 | 0.038 | 40 |
| Homo sapiens MAD-related gene SMAD7 (SMAD7) mRNA, complete cds | 3.829 | 0.025 | 79 |
| Human ETS2 oncogene | 2.260 | 0.026 | 80 |
| Human Bcl-2 related (Bfl-1) mRNA, complete cds | 0.472 | 0.008 | 98 |
| Protein kinases | | | |
| Non-catalytic region of tyrosine kinase | 0.233 | 0.022 | 29 |
| Erythrocyte membrane protein band 4.9 (dematin) | 0.408 | 0.041 | 45 |
| Human mRNA for TESK1, complete cds | 0.282 | 0.030 | 82 |
| H. sapiens mRNA for Ndr protein kinase | 0.435 | 0.043 | 94 |
| signal transduction | | | |
| Calcineurin B | 0.318 | 0.021 | 21 |
| JNK activating kinase 1 | 0.170 | 0.011 | 27 |
| Calreticulin Precursor | 12.868 | 0.017 | 31 |
| Human heregulin-beta1 gene, complete cds | 5.582 | 0.030 | 50 |
| Transcription | | | |
| Homo sapiens NF-E2 protein (NF-E2) mRNA, complete cds | 2.223 | 0.048 | 8 |
| Evi-1 | 0.159 | 0.032 | 58 |
| Human TFIIB related factor hBRF (HBRF) mRNA, complete cds | 0.118 | 0.025 | 66 |
| Human melanocyte-specific gene 1 (msg1) mRNA, complete cds | 0.390 | 0.028 | 68 |
| COUP transcription factor | 0.080 | 0.003 | 73 |
| Human CREB-binding protein (CBP) mRNA, complete cds | 0.210 | 0.025 | 106 |

TABLE 1-continued

Potentially regulated genes by category.
Numbers correspond to FIG. 7.

| Gene/Category | Ratio | P Value | No. |
|---|---|---|---|
| Transport/carriers | | | |
| Hemoglobin, alpha 1 | 0.157 | 0.017 | 3 |
| H. sapiens mRNA for translin associated protein X | 2.631 | 0.043 | 25 |
| Human transportin (TRN) mRNA, complete cds | 3.328 | 0.026 | 32 |
| Hemoglobin zeta chain | 11.817 | 0.036 | 91 |

TABLE 2

Genes exhibiting a high ratio of up-regulation.

| Gene | Number |
|---|---|
| Homo sapiens cdc14 homolog mRNA, complete cds | 63 |
| Homo sapiens mRNA for ISLR, complete cds | 41 |
| Collagen, type IX, alpha 3 | 28 |
| Calreticulin presursor | 31 |
| Hemoglobin zeta chain | 91 |

TABLE 3

Genes exhibiting a high ratio of down-regulation.

| Gene | Number |
|---|---|
| Villin | 47 |
| Homo sapiens thrombospondin 3 (THBS3) gene, complete | 59 |
| Homo sapiens mRNA for transducin (beta) like 1 protein | 97 |
| Adenylate kinase 1 | 10 |
| Oxytocin receptor | 11 |

EXAMPLE 2

PCR Results

Two genes with opposing expression differentials (one up-regulated [Number 22, Table 1], one down-regulated [Number 21, Table 1]) were chosen for verification by the PCR analysis. The genes were selected to incorporate low P values, similar expression ratios, and similar expression intensities, avoiding pairs with marginal statistical significance.

Figure 8:
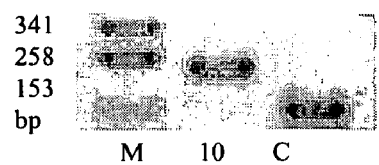
FIG. 8 shows PCR amplification of reference sequences. M, marker (DpnI digest of pUC18); 10, cdc10; C, calcineurin. The marker indicates that the lengths of the sequences are correct (253 and 150 bp).
Figure 9A:
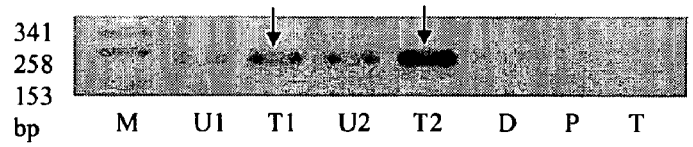
FIGS. 9A and 9B show PHA-mediated up-regulation of cdc10 (FIG. 9A) and down-regulation of calcineurin B (FIG. 9B) in *Axinella corrugata* cell cultures. 1, specimen 1; 2, specimen 2; U, untreated; T, PHA treated; D, reverse transcriptase-free DNA control; P, template-free control; T, primer-free control; M, DpnI digest of pUC18 (marker).
Figure 9B:
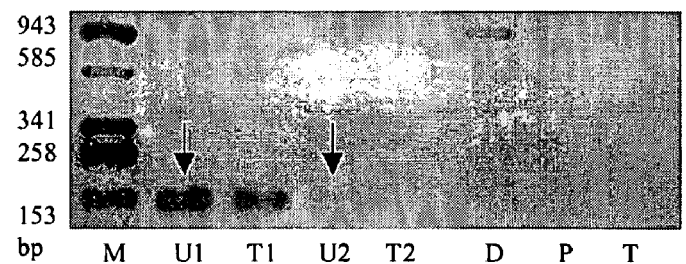

FIG. 8 shows the results for PCR amplification of the reference sequences from the plasmid DNA for the I.M.A.G.E. (human) clone. The products appear at the correct locations for their predicted size. FIG. 9 displays the results for the PCR analysis of the same two genes, a cdc10 homologue and a calcineurin subunit, in A. corrugata. The microarray analysis indicated that cdc10 was up-regulated by the PHA treatment, while calcineurin was down-regulated, each approximately 2–5 fold. PCR results support this finding, with visibly more product seen in the appropriate lane (noted by arrow) for each of the paired samples. The background contribution of genomic DNA is minimal for cdc10, which produced a very faint band in lane D. For calcineurin B, the DNA background is irrelevant, since the length of the product in lane D indicates that the primers span an intron and produce a band impossible to confuse with the target. The figure also shows results for negative controls lacking primers and template, confirming that the results are not due to reagent contamination.

The subject invention pertains, in part, to the discovery that PHA-mediated gene expression regulation occurs in sponge cell cultures.

Figure 10:
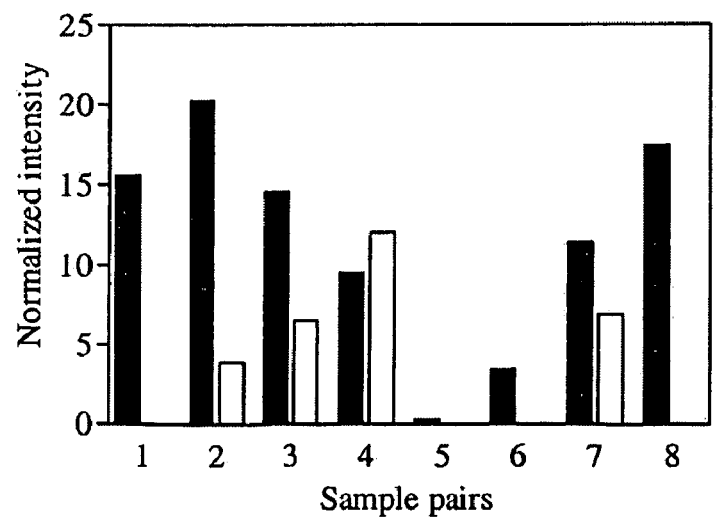
FIG. 10 shows normalized calcineurin B expression intensities for 8 individual sample pairs. Dark bars, untreated; open bars, PHA treated. A single intensity value is represented by each bar. Note reversed ratio for the fourth pair of bars. The intensities of 4 PHA bars are too low to be visible on this histogram. P=0.021.

The data for a regulated gene, focusing on the individual pairs of sponge cultures, confirms the PHA-induced trend of down-regulation for calcineurin B (FIG. 10) and a PHA-induced trend of up-regulation for CDC-10.

The populations have exhibited different means, with many data points in the up-regulated population far exceeding the ranges of the down-regulated population. Gene expression differences between treated and untreated sponge cell cultures were observed, using cross-species hybridization to a microarray of human gene sequences.

EXAMPLE 3

Statistical Methods

The paired t test was chosen for this analysis, though it is likely that a non-parametric test might be appropriate for some of the genes. Applying individualized tests for each of the genes would diminish the advantages of working with microarrays. In addition, the log transformation helps to normalize the data (Zar 1974 supra) and improve the function of the paired t test (Motulsky 1995 supra). Therefore, the powerful t test functioned as desired for this study, and selection of a relatively high P value threshold, considering the high number of parallel tests being conducted, serves to reduce the data pool to a manageable size.

Homologies and Differentials. The number of homologies is indicated by the intensely hybridized spots on the sponge-human microarrays, even with the higher stringency wash protocol.

EXAMPLE 4

The present invention provides a panel of 108 genes displaying up- or down-regulation in sponge cell cultures stimulated with PHA for 12 hours. Two of these genes were selected for further analysis by PCR.

Calcineurin B (Number 21, Table 1) and the human homologue of Saccharomyces cerevisiae cdc10 (Number 22, Table 1) were subjected to PCR verification. Primers designed to match the human sequences worked for both the sponge and human templates.

The interplay between calcium and calcineurin signaling may provide clues to influencing the sponge cell cycle via calcium and/or calcineurin.

Cdc10. Transcript levels of cdc10 generally have not been considered relevant to cell cycle control, yet this study finds elevated expression associated with the PHA treatment. Some work has been done on cdc10 expression, including a study which documented reduced expression of cdc10 in astrocytomas (Huang H, Colella S, Kurrer M, Yonekawa Y, Kleihues P, Ohgaki H. 2000. Gene expression profiling of low-grade diffuse astrocytomas by cDNA arrays. Cancer Res 60(24):6868–6874), and elevated expression associated with favorable prognoses in neuroblastoma (Nagata T, Takahashi Y, Asai S, Ishii Y, Mugishima H, Suzuki T, Chin M, Harada K, Koshinga S, Ishikawa K. 2000. The high level of hCDC10 gene expression in neuroblastoma may be associated with favorable characteristics of the tumor. J Surg Res 92(2):267–275), both of which suggest a link between elevated expression and reduced replication—findings contrary to those reported here. In contrast, there is some precedent for regulation of cdc10 transcription, reported by Kaback and Feldberg (Kaback DB, Feldberg LR. 1985. *Saccharomyces cerevisiae* exhibits a sporulation-specific temporal pattern of transcript accumulation. Mol Cell Biol 5(4):751–761). They quantified cdc10 transcripts in sporulating and vegetative yeast, documenting increased transcript abundance in the sporulating cells.

Though constitutive expression of cdc10 is an accepted interpretation, one can intuitively conceive of a reasonable scenario of regulation. If cdc10 is required to complete the cell cycle, then it might be absent in resting cells or present in greater quantities in stimulated cells. It is possible the quiescent cells had ceased producing cdc10.

Other potentially regulated genes. Of the remaining 106 potentially regulated genes detected in this research, 30 are up-regulated by the PHA treatment. Of these, several are highly indicative of mitogenesis and/or consistent with the known action of PHA in model systems. The apparent up-regulation of the alpha chain of interleukin 15 (IL-15) receptor (Number 54, Table 1) is an example. IL-15 is a pro-inflammatory molecule that acts as a growth factor in T cells (Handisurya, A. et al. 2001, *Prostate* 49(4):251–262). It has anti-apoptotic effects (Rappl, G. et al. 2001, *Cell Death Differ* (4):395–402) and is associated with tumor propagation (Tinhofer, I. et al. 2000, *Blood* 95(2):610–618). Equally interesting is the potential up-regulation of a sub-unit of interleukin 12 (Number 86, Table 1). Since reduced transcription of this product has been attributed to NFκB down-regulation, the inverse observation noted in this study could be predicted in the context of T cell activation with concomitant NFκB activation. Up-regulation of these genes underscores the similarity between sponge archaeocytes (Bergquist PR. 1979. Sponges. Hutchinson. 268 p), the primary, stem-cell-like cell type targeted for culture in these studies (Pomponi and Willoughby 1994 supra), and T cells.

Among the down-regulated genes, a potential reduction in villin (Number 47, Table 1) transcripts exhibited an extremely significant P value and a high expression ratio. The converse situation (increased expression of villin) is consistent with reduced growth and increased differentiation in colon cancer cells (Kitamura, S. et al. 1999, *Jpn J Cancer Res* 90(1):75–80), so up-regulation in cultures displaying improved growth is consistent. Once again, the scenario supports logical and profound effects of PHA on sponge cells in vitro.

In a more general sense, the ubiquity of calcium signals is once again evident in the apparent up-regulation of sponge calreticulin (Number 31, Table 1) by PHA. Membrane expression of calreticulin is associated with T cell activation (Arosa, F. A. et al. 1999, *J Biol Chem* 274(24):16917–16922). Furthermore, the protein is abundantly expressed in hypertrophic fibroblasts (Zhao Y, He Q. 1999. Study on the expression of calreticulin in hypertrophic scar-derived fibroblasts. Zhonghua Zheng Xing Shao Shang Wai Ke Za Zhi 15(3):167–169). Both of these demonstrated scenarios can be interpreted as consistent with cell growth and proliferation. However, calreticulin up-regulation is also associated with promotion of apoptosis (Kageyama, K. et al., *J Biol Chem* 2002 [epub ahead of print].), a finding contrary to the desired effects in development of sponge cell cultures. A still different perspective on calreticulin function interprets its role as potentially beneficial, and clearly linked to calcium signaling (a known major factor in PHA action). Research in plants, in particular, has shown that the very high $Ca^{2+}$ binding capacity of calreticulin may function to increase calcium stores in the endoplasmic reticulum (Wyatt, S. E. Tsou, P. L. and D. Robertson 2002, *Transgenic Res* 11(1):1–10), possibly enhancing cell survival in stress situations, including growth medium calcium deficiency (Persson, S. et al. 2001, *Plant Physiol* 126(3):1092–1104.). This is noteworthy in light of the facts that sponge cells are briefly suspended in calcium-free medium during dissociation, and the calcium adequacy of the subsequent growth medium is uncertain. Calreticulin up-regulation in PHA-treated sponge cells may be even more intriguing in view of the apparent concurrent down-regulation of the COUP transcription factor (Number 73, Table 1), which is known to suppress calreticulin transcription (Guo, L. et al. 2001, *J Biol Chem* 276(4):2797–2801). The concordance of these two findings supports their legitimacy and reinforces the possibly critical role of calcium in improvement of sponge cell cultures.

Among the PHA-regulated genes, several suggest involvement of oncogenic and/or anti-apoptotic functions in the observed stimulation of sponge cells. Since expression of alpha-catenin (Number 81, Table 1) can confer resistance to certain apoptosis inducers (Matsubara, S. and M. Ozawa 2001, *J Cell Biol* 154(3):573–584), its up-regulation in sponge cell cultures (as suggested in this study) may be desirable. The possible regulation of this extracellular matrix (ECM)-related protein also highlights the likely role of ECM signal deprivation in the inhibition of proliferation in sponge cell cultures. The apparent up-regulation of ETS2 (Number 80, Table 1) is not surprising, since this is a demonstrated phenomenon in T cell activation (Bhat, N. K. et al. 1990, *Proc Natl Acad Sci USA* 87(10):3723–3727). Though ETS2 has been categorized as an oncogene (Santoro, A. et al. 1992, *Cancer Genet Cytogenet* 58(1):71–75), it has also been associated with anti-transforming action (Foos, G. et al. 1998, *J Biol Chem* 273(30):18871–18880). However, Sementchenko et al. 1998 (*Oncogene* 17(22): 2883–2888) demonstrated a positive association between ETS2 and transformation. The protein is also associated with inhibition of apoptosis (Sevilla, L. et al. 1999, *Mol Cell Biol* 4:2624–2634). Clearly, the observed PHA-induced up-regulation of a putative oncogene is logical, and potentially beneficial, in the effort to produce a sponge cell line. Returning to the potential role of anti-apoptotic regulation, this type of action is again suggested by possible down-regulation of TIA-1 Number 40, Table 1), an apoptosis-promoting protein (Forch and Valcarcel 2001). Phosphorylation of TIA-1 precedes DNA fragmentation and is thought to be instrumental in fas-mediated apoptosis (Tian, Q. et al. 1995, *J Exp Med* 182(3):865–874.).

Some of the genes exhibited relatively large expression ratios, as indicated in Tables 2 and 3. Of the up-regulated genes (Table 2), cdc14 may be the most interesting. Since it functions in late mitosis (Shou, W. et al. 1999, *Cell* 97(2): 233–244), it is another indicator of proliferative effects of PHA. The type IX collagens, which have been identified as conserved in marine invertebrates (Tanzer, M. L. et al. 1993, *Connect Tissue Res* 29(2):111–117), have been associated with development, particularly chondrogenesis (Kulyk, W. M., C. N. Coelho and R. A. Kosher1991, *Matrix* 11(4): 282–288). The ISLR gene is a cell surface antigen found to be up-regulated concurrent with expression of a specific proto-oncogene during retinoic acid treatment (Tice, D. A. et al. 2002, *J Biol Chem* 277(16):14329–14335). Therefore, up-regulation of any of these genes is not surprising in the context of PHA stimulation. The role of a hemoglobin is less suggestive, so a functional summary is not included here.

The table of genes with high ratios for down-regulation (Table 3), includes oxytocin. The finding that the COUP transcription factor may participate in regulation of oxytocin expression (Ivell, R. R. A. Bathgate, N. Walther and T. Kimura 1998, *Adv Exp Med Biol* 449:297–306) makes the observation more important. Since COUP transcription factor levels appear to be concurrently reduced, expression levels for the two genes may be related. Though adenylate kinase is generally viewed from a metabolic perspective, there is some evidence it may also play a role in growth regulation (Collavin, L. et al. 1999, *Oncogene* 18(43): 5879–5888). Either role may be relevant to PHA stimulation of the cells. Roles for thrombospondin or transducin are more difficult to characterize, and are not summarized here.

EXAMPLE 5

Mammalian Comparisons

Of the high-ratio genes listed in Tables 2 and 3, as well as those genes mentioned in this discussion, only one (COUP transcription factor), exhibited significant regulation in the murine cells. Furthermore, the gene was oppositely regulated, exhibiting a higher signal in the PHA-treated murine cells.

Sponges represent a very simplified version of a multicellular animal, and the use of mammalian (human) arrays has permitted direct hybridization of many gene sequences common to both primary and advanced metazoans. Such comparisons can provide new insights into human health-related issues, based upon the function of specific genes in the comparatively simple sponge system.

A role of calcineurin down-regulation in enhancement of sponge cells cultures was observed. Future efforts to improve sponge cell culture through manipulation of calcium concentrations or calcium signaling pathways may be important.

Perhaps the most important suggestive feature of these data is that the control of apoptosis may play a major role in the sponge cell cultures. Apoptosis inhibition is often routinely intertwined with cell cycle progression, but may be even more pointedly significant in this case. Control of apoptosis may be a starting point for promoting and prolonging the growth of sponge cells in vitro.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

We claim:

1. A method for evaluating gene expression wherein said method comprises treating an in vitro culture of marine sponge cells with a stimulus and assessing changes in gene expression resulting from the treatment with said stimulus;
wherein said method comprises generating labeled polynucleotide molecules corresponding to sponge genes having changes in expression resulting from the treatment with said stimulus;
and wherein said method further comprises applying said labeled molecules to a microarray having immobilized human genes to evaluate gene expression.

2. The method, according to claim 1, wherein said stimulus is phytohemagglutinin (PHA).

3. The method, according to claim 2, wherein said culture is stimulated with PHA for about 12 hours.

4. A method for identifying a gene, expression of which is regulated by a stimulus, the method comprising:
   a. subjecting a marine sponge in vitro cell culture to a stimulus;
   b. thereafter assessing the level of expression of the gene in the cell culture; and
   c. comparing the level of expression of the gene in the first cell culture with the level of expression of the same gene in a second cell culture, the second culture not being subjected to the stimulus;
whereby a difference between the level of expression of the gene in the first cell culture and the level of expression of the gene in the second cell culture is an indication that the gene is regulated by the stimulus;
wherein said method further comprises generating labeled polynucleotide molecules corresponding to sponge genes having changes in expression resulting from the treatment with said stimulus, and wherein said method further comprises applying said labeled molecules to a microrray having immobilized human genes to identify human gene homologues of the sponge genes.

5. The method, according to claim 4, wherein the sponge is *Axinella corrugata*.

6. The method, according to claim 4, wherein phytohemaggutinin (PHA) is administered to the cells, and changes in gene expression resulting from said treatment with PHA are assessed.

7. The method, according to claim 6, wherein said cultures are exposed to PHA for about 12 hours.

8. The method, according to claim 4, wherein the level of gene expression is compared by transcriptional profiling following microarray analysis using a radiolabeled probe.

9. The method, according to claim 4, wherein the levels of expression of at least ten genes are compared.

* * * * *